United States Patent
Loftman et al.

(10) Patent No.: US 6,679,844 B2
(45) Date of Patent: Jan. 20, 2004

(54) AUTOMATIC GAIN COMPENSATION FOR MULTIPLE MODE OR CONTRAST AGENT IMAGING

(75) Inventors: Rickard C. Loftman, Mountain View, CA (US); Ismayil M. Guracar, Redwood City, CA (US); Patrick J. Phillips, Sunnyvale, CA (US); Zafer Zamboglu, Mountain View, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 10/176,274

(22) Filed: Jun. 20, 2002

(65) Prior Publication Data

US 2003/0236459 A1 Dec. 25, 2003

(51) Int. Cl.[7] ................................................ A61B 8/00
(52) U.S. Cl. ......................... 600/443; 600/458; 73/631
(58) Field of Search ................... 73/631, 549; 600/437, 600/442, 443, 447, 440; 382/128–130

(56) References Cited

U.S. PATENT DOCUMENTS

| | | | |
|---|---|---|---|
| 5,442,462 A | * | 8/1995 | Guissin ....................... 358/463 |
| 5,577,505 A | | 11/1996 | Brock-Fisher et al. |
| 5,579,768 A | | 12/1996 | Klesenski |
| 5,632,277 A | | 5/1997 | Chapman et al. |
| 5,891,038 A | * | 4/1999 | Seyed-Boloforosh et al. .... 600/447 |
| 5,902,242 A | * | 5/1999 | Ustuner et al. ............. 600/443 |
| 5,910,115 A | | 6/1999 | Rigby |
| 5,951,478 A | | 9/1999 | Hwang et al. |
| 5,993,392 A | | 11/1999 | Roundhill et al. |
| 6,095,980 A | | 8/2000 | Burns et al. |
| 6,176,830 B1 | * | 1/2001 | Freiburger .................. 600/453 |
| 6,221,020 B1 | * | 4/2001 | Lysyansky et al. ......... 600/453 |
| 6,283,919 B1 | * | 9/2001 | Roundhill et al. .......... 600/447 |
| 6,352,511 B1 | * | 3/2002 | Hossack et al. ............ 600/443 |
| 6,398,733 B1 | | 6/2002 | Simpoulos et al. |
| 6,436,046 B1 | * | 8/2002 | Napolitano et al. ......... 600/447 |
| 6,454,714 B1 | * | 9/2002 | Ng et al. .................... 600/443 |
| 6,458,083 B1 | * | 10/2002 | Jago et al. .................. 600/443 |

* cited by examiner

Primary Examiner—Francis J. Jaworski

(57) ABSTRACT

The gain for multiple mode imaging and/or contrast agent imaging is automatically adjusted. The gain algorithm separately determines gain parameters for two different types of imaging, such as tissue and contrast agent imaging. The gain based on the contrast agent image may be optimized to provide maximum sensitivity, such as by mapping noise values measured prior to injection of contrast agent to low values within the dynamic range or somewhat below the display dynamic range. The automatic gain based on the contrast agent image may be free of variance calculations. One of the two gain parameters is selected as the system gain, or the two gain parameters are combined to form the system gain. The presence of contrast agents within the image may be determined, and different gain parameters used based on the presence or absence of contrast agents. Various ones or combinations of the gain adjustments summarized above may be used.

31 Claims, 4 Drawing Sheets

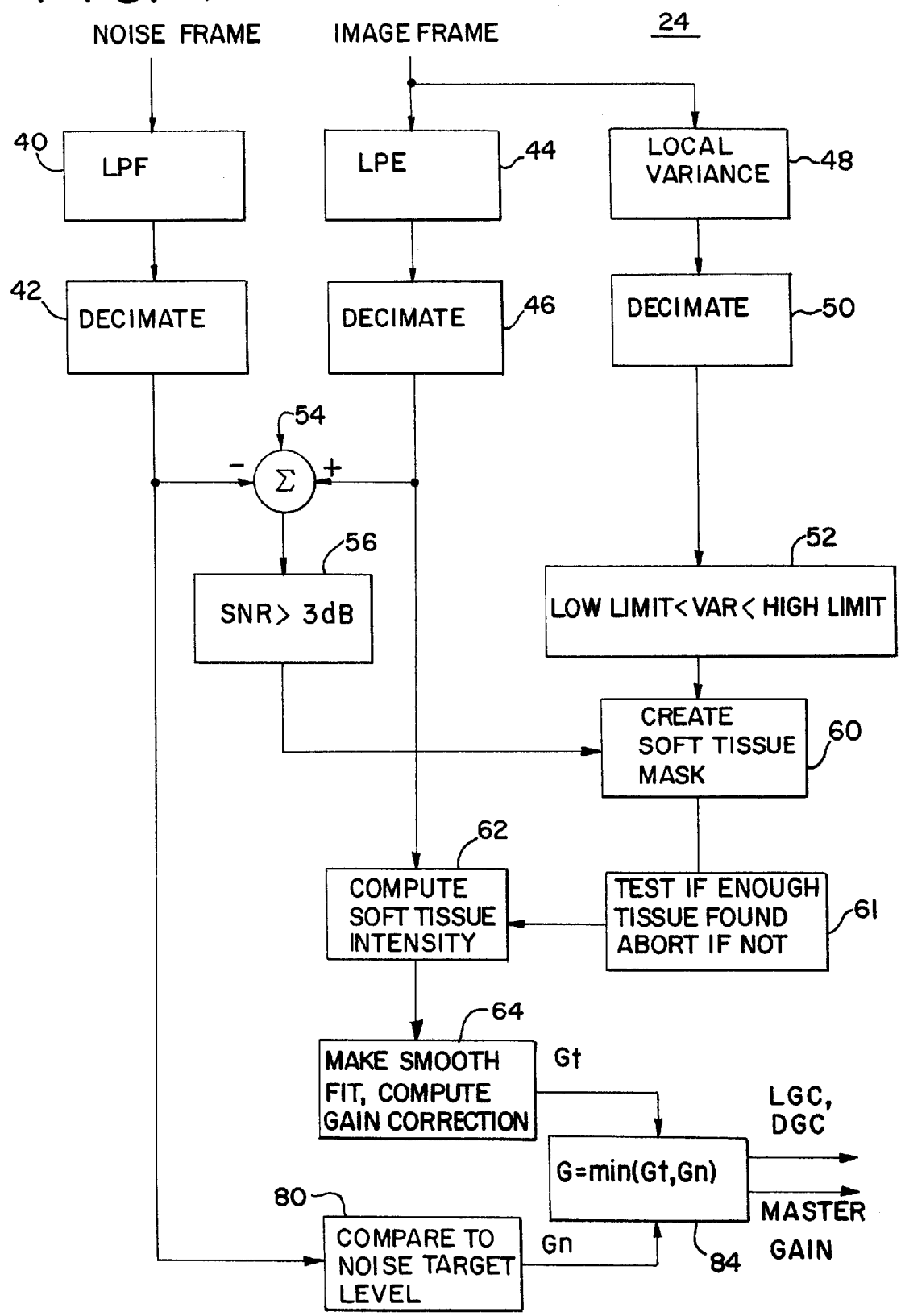

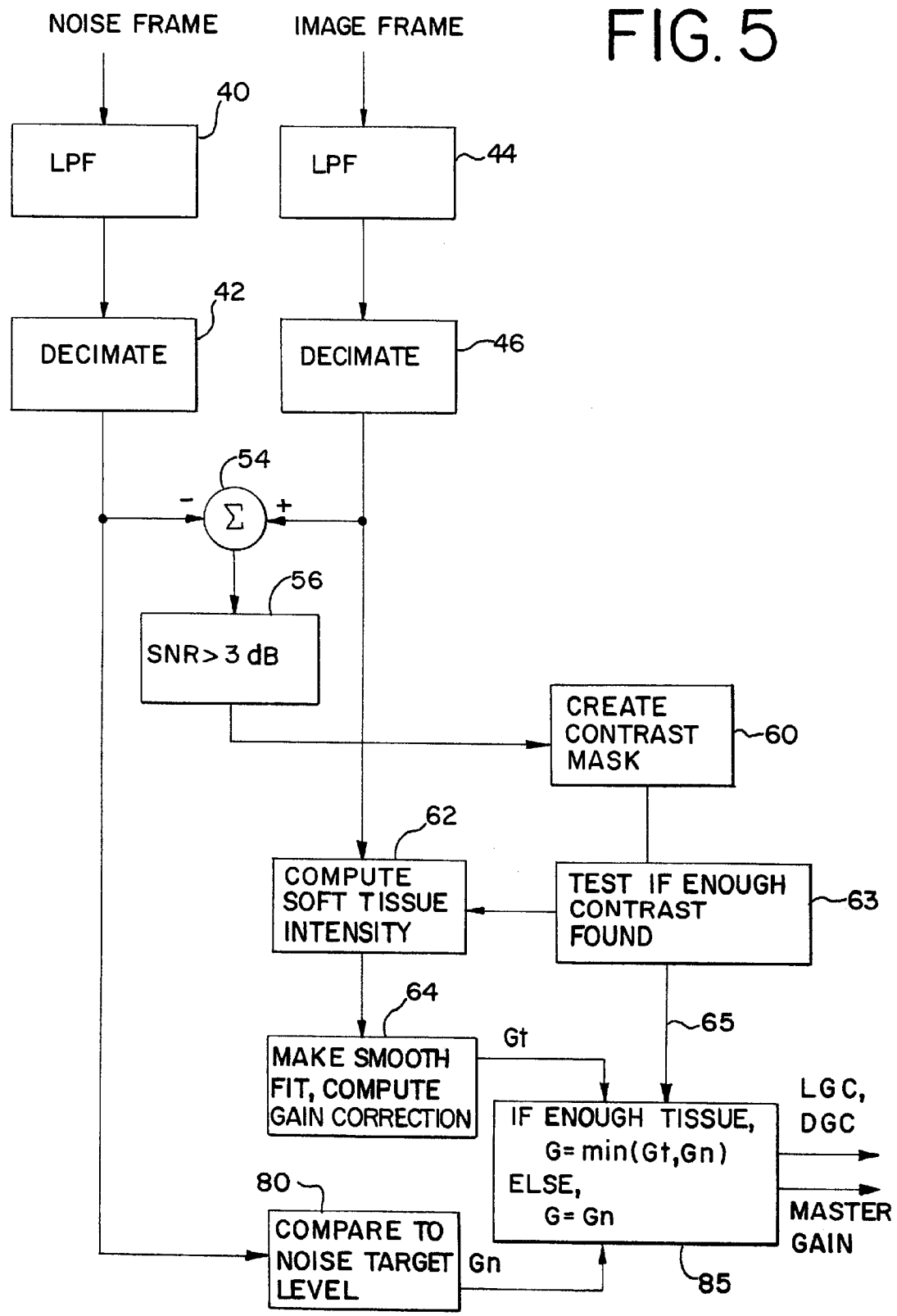

AUTOMATIC GAIN COMPENSATION FOR MULTIPLE MODE OR CONTRAST AGENT IMAGING

BACKGROUND

The present invention relates to medical diagnostic ultrasonic imaging, and in particular to systems that adaptively set gain to improve such imaging.

In conventional ultrasonic imaging, a B-mode image signal is adjusted for gain before the signal is mapped to a range of gray levels or colors for display. The gain can conventionally be varied by the user using a depth gain compensation (DGC) or a time gain compensation (TGC) control along with the master gain or B gain control. The DGC and TGC controls are conventionally variable in range only, and the master gain is independent of both range and azimuthal position. However, a lateral gain (LGC) may also be used.

Commercially available one-dimensional gain controls are often used by users to adjust brightness level. In many cases, users adjust the gain mainly to keep the regional mean of the soft tissue gray level within a narrow range of gray values. This preferred range is somewhat consistent from user to user, and in many cases users tend to adjust the gain to set the gray level for soft tissue to the 64th gray level on a linear map that maps 0 to black and 255 to white. However, gain adjustments for soft tissue brightness uniformity do not simultaneously optimize noise suppression and avoidance of saturation effects. Manual gain adjustments take time and require user expertise. Gain is frequently sub-optimal for some or all parts of an image. As a result, information can be lost by cutting off low-level signals or saturating high-level signals.

Various automatic gain setting algorithms have been used. One example is provided for color Doppler energy imaging. A measurement of the thermal noise along a center line is used to set the gain dependence on depth which can provide maximum signal sensitivity regardless of signals responsive to the transmission of acoustic energy. The user cannot adjust this gain, and the gain is not optimized as a function of multiple dimensions.

To more optimally control gain, U.S. Pat. No. 6,398,733 (assigned to the assignee of the present invention) discloses adaptively setting gain for a B-mode image. Spatial variance is used to identify regions of the image corresponding substantially to soft tissue. The system acquires a noise frame with the transmitters turned off, and then uses the noise frame and the identified regions of soft tissue both to locally and adaptively set the gain to cause soft tissue to be displayed at a constant average level throughout the image.

Optimal gain settings are different for imaging contrast agents. The target brightness may be manually adjusted for second harmonic B-mode contrast agent imaging. Gain optimization is important but difficult for imaging contrast agents. Contrast agent imaging may use low transmit powers, making setting the gain for adequate sensitivity difficult. Signal from tissue may be included in the contrast agent image, so the gain may reduce contrast between contrast agents and tissue. Some contrast agent imaging protocols require brightness level comparison, requiring that the gain not be adjusted from before contrast agents are injected, or at least during the course of agent uptake into or outflow from tissue.

The various gain setting techniques discussed above for tissue imaging may be sub-optimal for other types of imaging, such as contrast agent imaging, and vice versa. Several different types of imaging are frequently used for imaging contrast agents, such as one image generated to represent contrast agents and another image generated to represent tissue. The contrast agent and tissue images are displayed separately or one overlaid on the other. The same gain curve may be applied for both images. Setting a gain curve based on the tissue image results in a poor gain curve for the contrast agent image. Gain setting algorithms adapted for identifying soft tissue may not be robust or optimal for the gain of the contrast agent image. The character of contrast agent images differs from tissue images. Since contrast agent imaging typically begins before introduction of contrast agent, any initial gain settings may be improper after administration of the contrast agent. Prior to the administration of contrast agent, automatic gain settings based on the contrast agent image may fail due to a lack of signal.

BRIEF SUMMARY

The present invention is defined by the following claims, and nothing in this section should be taken as a limitation on those claims. By way of introduction, the preferred embodiments described below include methods and systems for automatically adjusting the gain for multiple mode imaging and/or contrast agent imaging. The gain algorithm separately determines gain parameters for two different types of imaging, such as tissue and contrast agent imaging. The gain based on the contrast agent image may be optimized to provide maximum sensitivity, such as by mapping noise values measured prior to injection of contrast agent to low values within the dynamic range. The automatic gain based on the contrast agent image may be free of variance calculations. One of the two gain parameters is selected as the system gain, or the two gain parameters are combined to form the system gain. The presence of contrast agents within the image may be determined, and different gain parameters used based on the presence or absence of contrast agents.

Various ones or combinations of the gain adjustments summarized above may be used. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIG. 4 is a flow chart diagram of one embodiment of a method for determining gain for tissue imaging.

FIG. 5 is a flow chart diagram of another embodiment of a method for determining gain for contrast agent imaging.

DETAILED DESCRIPTION OF THE PREFERRED EMBODIMENTS

Figure 1:
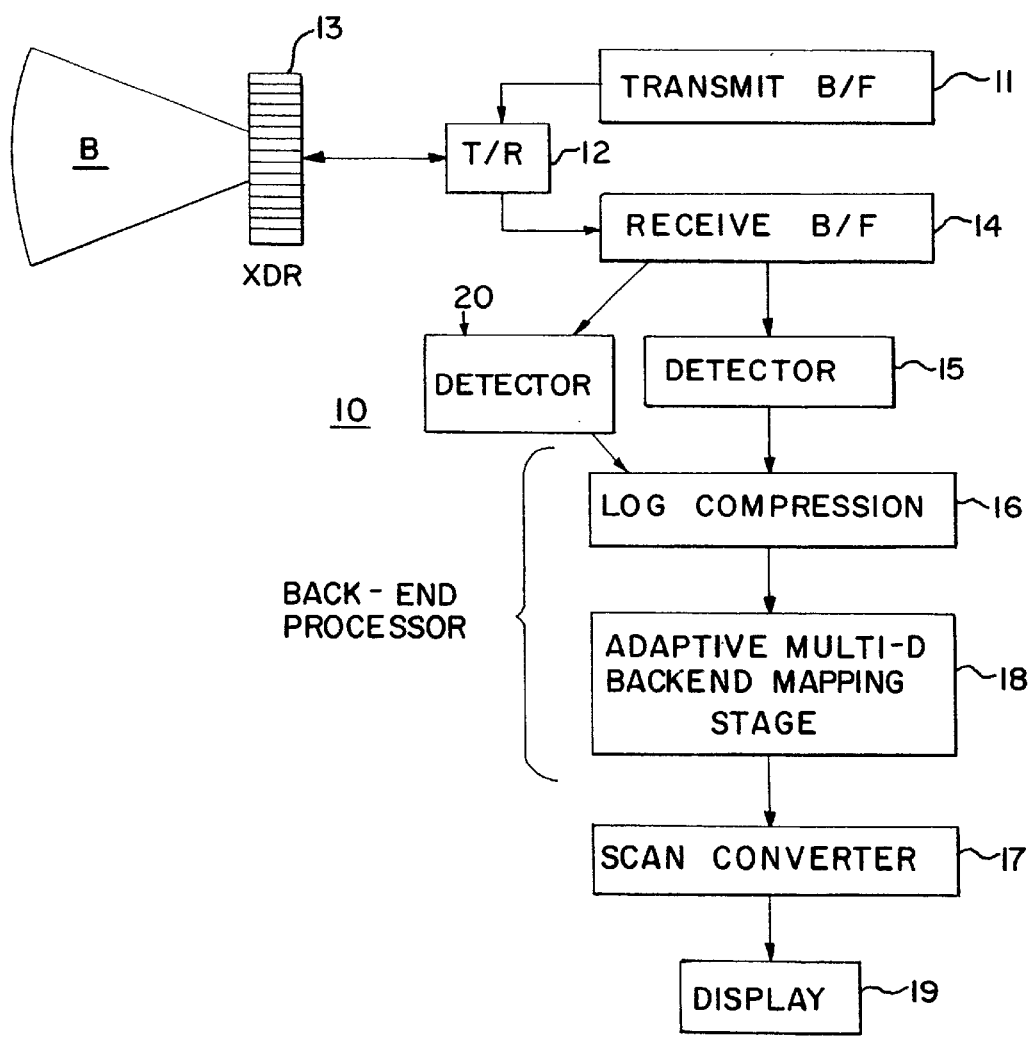
FIG. 1 is a block diagram of one embodiment of an imaging system with automatic gain control.

FIG. 1 shows a block diagram of a medical diagnostic ultrasonic imaging system 10 for adaptively controlling gain in a dual mode or contrast agent image. As shown in FIG. 1, a transmit beamformer 11 applies transmit waveforms via a transmit/receive switch 12 to a transducer array 13. The transducer array 13 produces ultrasonic pulses in response to the transmit waveforms, which pulses are directed into a field of view of a body B to be imaged. Returning echoes from the body B impinge upon the transducer array 13, which converts these echoes into receive signals that are transmitted via the transmit/switch 12 to a receive beamformer 14. The receive beamformer 14 applies appropriate delays and phase shifts to cause the receive signals from selected locations within the body B to add coherently.

These beamformed signals are applied to one or both of detectors 15, 20. The different detectors 15, 20 are used for different types of imaging. Different types of imaging use different transmit and associated receive sequences (e.g. single pulse versus multiple pulse), like transmit and different receive sequences (e.g. sharing at least one a transmit pulse for different receive combinations), different filters (e.g. removing fundamental versus harmonic information), different weights (e.g. no interpulse amplitude modulation versus interpulse amplitude modulation), different types of detection (e.g. intensity verses energy) or other imaging attribute.

In one embodiment; one detector 15 comprises a B-mode or amplitude detector. The detector 15 detects tissue information, but may also detect contrast agent, movement or other structure. The detector 15 detects fundamental frequency, second harmonic or other harmonic information responsive to a single transmission or multiple transmissions and associated receive signals.

The other detector 20 comprises an amplitude detector operating to determine contrast agent information using a method different from detector 15. For example, receive signals are combined and the result amplitude detected by a B-mode detector or a Doppler detector. The detector 20 detects contrast agent information. For example, any of the detectors and associated transmit and receive sequences disclosed in U.S. Pat. No. 6,494,841 (U.S. application Serial Nos. 09/514,803 and 09/650,942), the disclosures of which are incorporated herein by reference, are used. These detectors detect contrast agent information in response to different interpulse phase and/or amplitude modulation. Such detection methods may provide signals representing primarily contrast agent or contrast agent absent tissue information. In other embodiments, the detector 20 detects both contrast agents and tissue information, such as with single pulse or multi-pulse harmonic B-mode imaging. High power transmissions, low power transmissions or combinations of both may be used to avoid or cause destruction of contrast agent as part of imaging contrast agent. In one embodiment, contrast agent data is detected in response to multiple low power pulses with both interpulse amplitude and phase modulation.

The transmit and receive pulses for one detector 15 may be used for the other detector 20. For example, the detector 20 combines information responsive to three interpulse amplitude modulated transmit pulses with or without phase modulation. Echoes responsive to the one pulse are used by the detector 15 for B-mode tissue imaging. In other embodiments, additional, different or no pulses are shared by the two or more detectors 15, 20.

In alternative embodiments, only one detector 15, 20 is provided or used. The single detector 15, 20 sequentially detects data for two or more different types of imaging or only detects data for one type of imaging. For example, the detector 15, 20 detects both contrast agent and tissue information, such as detecting with a B-mode detector.

The detected information is provided to a back-end processor that includes a log compression device 16 and an adaptive multi-dimensional back-end mapping stage 18. The mapping stage automatically determines and applies an overall gain and/or a gain curve optimized for the type of imaging. The output of the back-end processor is applied to a scan converter 17. The scan converter 17 generates display values upon a grid appropriate for a display 19.

All of the elements 11–17 and 19 can take any suitable form, and are not limited to any particular implementation. For example, the transmit and receive beamformers can be constructed as analog or digital devices, and any suitable transducer array can be used, including a single-element transducer array and phased arrays of various dimensions. Also, the system 10 may include additional elements in the signal path between the transducer array 13 and the display 19, and selected ones of the illustrated elements may be deleted or the order of some of the elements may be switched. For example, the order of the back-end processor and scan converter 17 can be altered.

The system 10 responds to user input or a triggering event to automatically or adaptively set the gain for imaging. For example, the user presses a button to have the system 10 automatically set the gain. As another example, the system 10 automatically sets the gain in response to user selection of an imaging configuration, such as selecting a contrast agent imaging configuration. As yet another example, the gain setting is triggered in response to a detected event, such as the presence of contrast agent in an imaged field of view, or a time limit, such as setting the gain every second. The user may further adjust the gain by controlling potentiometers or knobs for an average brightness, lateral brightness or depth brightness. Separate or shared controls may be provided for multiple types of imaging.

In the system 10, the adaptive multi-dimensional back-end mapping stage 18 controls the gain. The mapping stage 18 comprises one or more processors, filters, application specific integrated circuits, digital signal processors, analog components, digital components and combinations thereof. The mapping stage 18 can take many forms and in general automatically determines an overall, average or master gain as well as a lateral/depth gain curve. The mapping stage 18 sets and applies a brightness level for spatial locations within an image. In alternative embodiments, the mapping stage 18 alters the amplitude of data prior to log compression or after scan conversion.

In one embodiment, the mapping stage 18 includes hardware devices and/or software algorithms for determining gain parameters for two or more different types of imaging. The gain parameters comprise a lateral gain curve, a depth gain curve, an average or overall gain, a value or values used to determine gain information or other parameter representing gain for one or more spatial locations.

Figure 2:
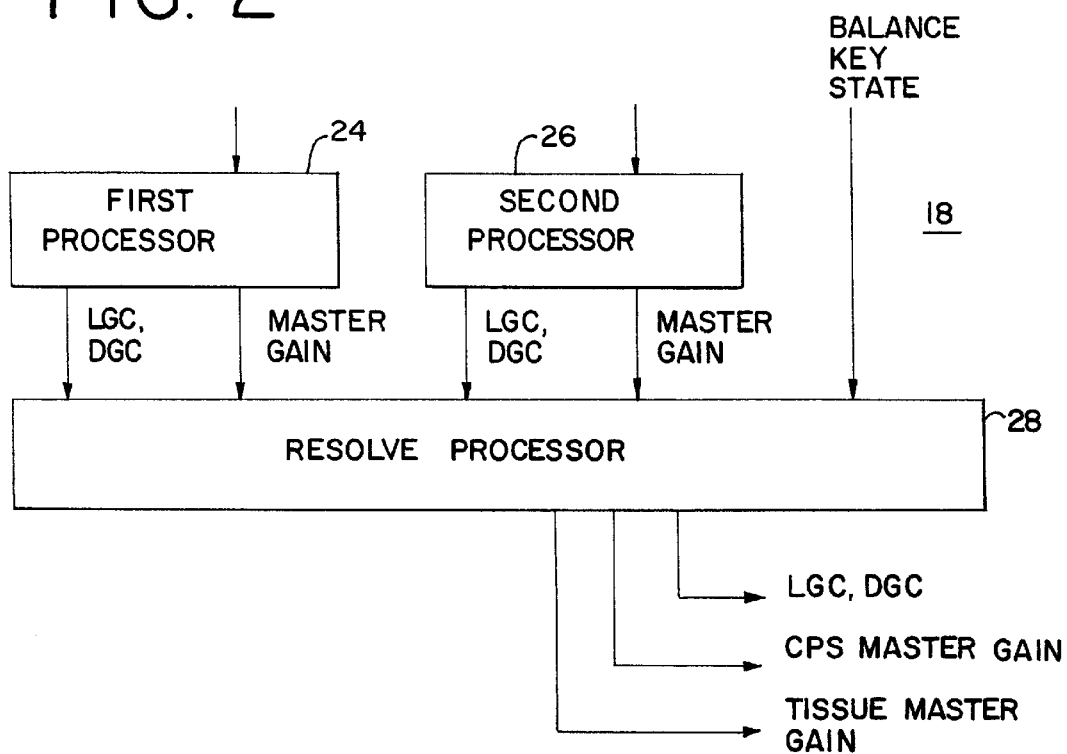
FIG. 2 is a block diagram of one embodiment of an automatic gain control system for multiple imaging modes.

FIG. 2 shows one embodiment of the mapping stage 18 for use with two different types of imaging. Two different processors 24 and 26 are implemented on the same or different hardware. One gain processor 24 determines gain parameters for a first type of imaging. The other gain processor 26 determines gain parameters for a second type of imaging. As shown, both two-dimensional or surface gain curves (LGC and DGC) and master or average gain are determined and output by both gain processors 24, 26. In alternative embodiments, different parameters are output or one gain processor 24 outputs a different type of parameter than the other gain processor 26.

A resolve processor 28 determines system or final gain information from the various gain parameters provided from the first and second gain processors 24, 26. The resolve processor 28 uses the same or different hardware as the first and second gain processors 24, 26. The resolve algorithm outputs both two-dimensional or surface gain curves (LGC and DGC) and a master or average gain for each of the two different types of imaging. In alternative embodiments, separate lateral and depth gain curves are output, only one gain parameter is output, only two gain parameters are output, a gain curve including spatially varying gain and the average gain, or other gain parameters are output.

In one embodiment, the two types of imaging used by the mapping stage 18 are contrast agent imaging and tissue imaging. Some contrast agent imaging techniques result in detected information representing contrast agents with minimal or almost no tissue information. The tissue image is displayed with the contrast agent image to provide reference tissue information prior to and during injection of contrast agents. The contrast agent image is overlaid on the tissue image, or the images are displayed separately. Different algorithms for determining gain allow automatic optimization of the gain algorithm based on the type of imaging. Gain algorithms are applied independently to data responsive to different types of imaging.

Figure 3:
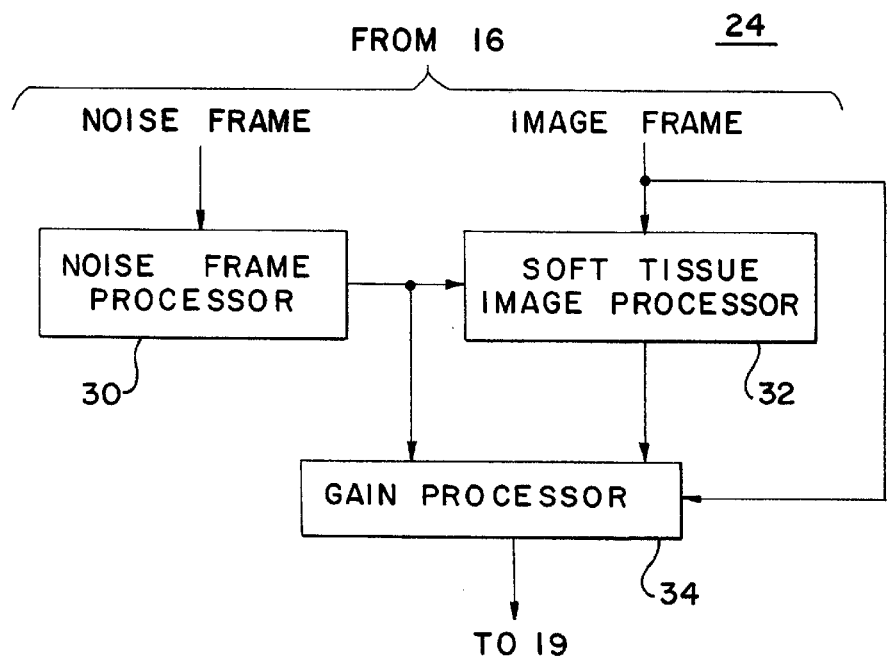
FIG. 3 is a block diagram of one embodiment of an automatic gain control system for a single imaging mode.

FIGS. 3 and 4 show one embodiment of implementation of the first processor 24 for use with tissue imaging. For example, the first processor 24 uses B-mode, second harmonic B-mode or other imaging techniques that provide tissue information alone or with other information. The embodiments described below in conjunction with FIGS. 3 and 4 determines a local gain in both the near field and far field of the tissue image such that soft tissue is displayed at a substantially constant target value. Other embodiments disclosed in U.S. Pat. No. 6,398,733, the disclosure of which is incorporated herein by reference, or other embodiments for determining gain parameters for tissue information may be used.

As shown in FIG. 3, the first processor 24 includes a noise frame processor 30, a soft tissue processor 32, and a gain processor 34. The noise frame processor 30 generates an estimate of electronic or thermal noise as the noise varies over the frame. The soft tissue processor 32 generates a smoothed surface indicative of the intensity of soft tissue within an image frame at various locations in the frame. The gain processor 34 uses outputs from the processors 30 and 32 to adaptively adjust or determine either the average gain, depth gain and/or lateral gain.

FIG. 4 provides a more detailed flow diagram of the one preferred embodiment of operation of the first processor 24 for determining gain from tissue data. Image acquisition parameters of the system 10 are set to pre-selected values. These pre-selected values optimize operation of the adaptive gain processor. By way of example, the following general guidelines have been found suitable in one embodiment: image acquisition parameters, including gain and dynamic range, are determined so that, for the widest possible variety of imaging situations, the highest possible signal-to-noise ratio (SNR) is maintained over the entire image without causing saturation of any portion of the image. This ensures that areas where the signal is weak are taken into account by the adaptive gain processor 34.

The noise processor 30 accepts as an input a noise frame, i.e. a frame of image data acquired with the transmitters turned off. Since the transmitters are turned off, there is not bona fide echo signal, and any signal appearing in the image frame is representative of system thermal or electronic noise. The noise frame is used to identify regions of image characterized by low SNR in conjunction with the creation of a SNR binary image.

A measure of average electronic noise at various locations distributed throughout the frame is generated. The noise frame of data is low pass filtered in act 40 and decimated in act 42. The low pass filtering smoothes the noise frame, and the decimation alters the filtered noise to a coarser gird, measuring, for example, 50 pixels on a side. This decimation is optional, and depends on system processing speed.

The tissue processor 32 accepts as an input a frame of data representing tissue. In act 44, the tissue data is low pass filtered. The low pass filtered data is decimated in act 46. In one embodiment, the acts 44 and 46 are identical to the corresponding acts 40 and 42.

The filtered, decimated noise frame is summed with negative polarity with the filtered, decimated image frame in act 54. Since the noise frame and the image frame are in this example post-detection, post-compression signals, the summation generates an output signal equal to the SNR for the associated region represented by the two frames of data. The SNR signal is compared to a threshold in act 56 to generate an SNR binary image. The SNR binary image is set equal to one in regions for the frame characterized by an SNR greater than a predetermined value, e.g. 3 dB, and to zero in regions where the SNR is less than or equal to the predetermined value. Thus, the SNR binary image identifies regions of the image frame that have a sufficiently high SNR to be candidates for soft tissue image signals. The portions of the SNR binary image characterized by the logic value zero correspond to the high-noise, low-SNR regions of the image, and these regions are not considered candidates for soft tissue.

The soft tissue processor 32 also generates a variance binary image by calculating a local variance of tissue data in act 48. In soft tissue, there are a large number of scatterers present in each resolution cell. Fully developed speckle occurs due to random interference between the reflected signals, and the amplitude of the signal obeys the Raleigh distribution in regions of the image frame depicting soft tissue. In this embodiment, the degree to which local variance, calculated in a few resolution cells around each image pixel, resembles that of fully developed speckle is used as a measure of the likelihood that a particular image pixel represents an image of a soft tissue.

In act 48, a statistical measure of variability is determined for select regions of the image frame. The spatial temporal mean of the amplitude-detected, log-compressed data can be used to determine variability. Alternately, the spatial variance of noise power normalized by the local mean of noise power can be used. For example, a normalized spatial variance can be determined on a pre-compression signal, where the normalized spatial variance is normalized by the local mean of the pre-compression signal. The statistical measure of variability may be calculated along any one of the lateral, axial, and elevation axis, any two of these axes, or all three axes. The image or frame of data is divided into a grid of smaller regions. The size of these regions is preferably on the order of ten times longer along each axis than the resolution size of the image. The spatial variance $V_{i,j}$ of the center of a region or cell C having the coordinates (i, j) can be calculated as follows:

$$V_{i,j} = \frac{1}{N^2} \sum_{k,l=1}^{N} (1_{i+k,j+l} - \langle 1 \rangle)^2.$$

The local variance is decimated in act 50. The decimation of act 50 preferably operates at the same scale as the decimation of acts 42 and 46. The decimated variance frame of data is then compared datum by datum with minimum and maximum variance levels in act 52. This comparison is particularly straightforward for log compressed data, where the variance of fully developed speckle characteristic of soft tissue is about $(5.57 \text{ dB})^2$. Thus, regions of soft tissue in the image frame will be characterized by fully developed speckle having a variance close to $(5.57 \text{ dB})^2$. For example, a variance is classified as characteristic of soft tissue if the variance meets the following relationship:

$$\left| \frac{\text{Var} - (5.57)^2}{(5.57)^2} \right| < 0.5.$$

The actual local variance of speckle may not be equal to the theoretical value due to filters in the signal processing path of the ultrasound systems. In practice, the variance is determined through measurements on phantoms mimicking soft tissue. The variance binary image is set equal to one in regions where the variance is consistent with soft tissue and to zero otherwise.

In act 60, a soft tissue mask is generated, such as by using an AND function. Both the SNR binary and variance binary frames of data are input for generating the soft tissue mask. Electronic noise has a variance close to that of soft tissue, and the AND operation uses the SNR binary image and the variance binary image to avoid misclassification of electronic noise as soft tissue. This AND operation is performed for each region of the decimated SNR binary image and the decimated variance binary image. The resulting decimated tissue binary image has a value equal to zero if either the SNR binary image indicates that the associated region is characterized by low SNR ratio or the variance binary image indicates that the associated region is not soft tissue. The SNR binary image is not required in all embodiments, and other techniques can be used to avoid misclassifying regions of the image dominated by noise as soft tissue. For example, noise reduction techniques can be applied prior to local variance estimation.

The local coherence factor may be used to ensure that regions of high acoustic noise or clutter are excluding from mapping decisions. The local coherence factor is defined as the ratio of the coherent (phase-sensitive) to the incoherent (phase-insensitive) summation across the receive channels of the delayed and apodized signals. See the discussion of Rigby, U.S. Pat. No. 5,910,115. A low coherence factor indicates strong phase aberration, i.e., high levels of acoustic noise or clutter. Therefore, using the coherence factor, the regions of the image dominated by clutter can be ignored.

As explained above, this soft issue identification can be done based on statistical measures of variability. Alternately, other methods may be used for identifying soft tissue, as for example methods based on the magnitude of the image signal. See the discussion of Klesenski, U.S. Pat. No. 5,579,768, assigned to the assignee of the present invention.

In act 61, the tissue binary image output from act 60 is tested for a sufficient number of tissue regions. For example, the decimated tissue binary image includes thirty six regions corresponding to a six-by-six grid. If at least one region in each of three laterally spaced columns and in each of three depth spaced rows are associated with tissue (i.e. at least six regions with specific distribution exist), a sufficient number of tissue regions exist. Other tests, numbers of regions, numbers of required tissue regions or no test may be used. If an insufficient number of tissue regions or spacing of tissue regions are identified, the gain process is ended or not completed for the tissue image.

If a sufficient number or spacing of tissue regions are identified, soft tissue intensities are computed in act 62. The filtered, decimated image frame of data output from act 46 and the binary tissue image frame of data output from act 60 are applied as inputs for computing soft tissue intensity. In particular, act 62 outputs a decimated frame having intensity values that depend upon the corresponding values of the tissue binary image in the same region. Where the corresponding region of the tissue binary image is equal to the logic value zero (indicating that the region does not correspond to soft tissue), the output does not include an intensity value for the corresponding region. Alternatively, for regions where the tissue binary image is equal to the logic value one, the output includes the intensity value for the corresponding region as filtered in act 44 and decimated in act 46.

In act 64, a gain parameter is determined. A surface, e.g., a second order surface, is fitted to the frame of data. This second order surface provides a measure of average soft tissue intensity as the intensity varies thought the image frame. Because of the use of the SNR binary image, portions of the image dominated by noise do not corrupt this second order surface. Because the surface is a second order surface fitted to a decimated frame, the surface does not vary so rapidly as to interfere with the presentation of transitions of interfaces between soft tissue of different contrasts. The difference between the fitted surface and a soft tissue target intensity level $T_t$ is calculated on a region-by-region or spatial location basis. The difference is a tissue gain $G_t$ which varies with both range and azimuth and is the gain required to cause the surface fitted to the local tissue mean to be displayed at the soft tissue target level $T_t$. In alternative embodiments, an offset representing an average difference for all or a sub-set of regions is calculated as a master tissue gain. The two-dimensional gain curve is then represented as a difference from the offset. Other values or calculations may be used to provide one or more gain parameters for each spatial location.

The low pass filtered, decimated noise frame of data from acts 40 and 42 is compared to a noise target value in act 80. A gain parameter signal $G_n$ is generated as the difference on a region-by-region or spatial location basis between a noise target level $T_n$ and corresponding values of the filtered, decimated noise frame. Thus, the noise gain $G_n$ also varies with both range and azimuth, and represents the gain that is required to ensure that the local mean noise level is presented at the noise target level $T_n$. In alternative embodiments, an offset representing an average difference for all or a sub-set of regions is calculated as a master noise gain. The two-dimensional gain curve is then represented as a difference from the offset. Other values or calculations may be used to provide one or more gain parameters for each spatial location.

In act 84, a final tissue two-dimensional gain parameter $G_f$ is determined. The minimum of the tissue gain $G_t$ and noise gain $G_n$ is selected for each spatial location or region. In one embodiment, an offset representing an average difference for all or a sub-set of regions of the final two-dimensional gain parameter is calculated as a master gain. The two-dimensional gain curve is then represented as a difference from the offset. For spatial locations away from the center of each region, the gain is interpolated based on the gain curve. Other values or calculations may be used to provide one or more gain parameters for each spatial location. The final gain $G_f$ is set so that tissue regions of the image are displayed at about the tissue target level $T_t$ for all portions of the image where the noise signal is less than the noise target level. In regions of the image where the noise intensity is greater than a noise target level $T_n$, a lower gain is used to ensure that noise is not amplified inappropriately. The local gain is varied adaptively to cause signals having the amplitude of the second order surface at the respective locations to be displayed as a soft tissue target value over some or all of the image.

The soft tissue target value can be set in many ways. The target display value may simply be a stored value or may be a user-selected value, or may be a value adaptively determined in response to ambient light. Alternatively, the soft tissue target level is a function of the currently invoked post-processing curve. Specifically, a user controllable or predefined value may be used as a target soft-tissue gray level $T_g$. $T_t$ is then defined whenever a post-processing curve is selected to be to be the signal intensity level that is mapped to the display gray level $T_g$.

Other algorithms using the same or different inputs and processes may be used for adaptively determining one or more gain parameters for tissue or other information. In alternative embodiments, one mode of imaging is used that includes both tissue and contrast agent information, so an algorithm adapted for contrast agents is used, such as discussed below.

The second processor 26 shown in FIG. 2 operates similarly to the first processor 24 as shown in FIGS. 2 and 3. Detected data responsive to a different type of imaging is input to the second processor 26. For example, the second processor 26 uses harmonic B-mode, loss-of-correlation, detection of non-linear fundamental, other multiple pulse detection techniques or other imaging techniques that primarily provide contrast agent information or provide contrast agent information with other information. A local gain in both the near field and far field of the contrast agent image is determined such that contrast agent is displayed at a substantially constant target value.

The second processor 26 is also implemented as shown in FIG. 3, except the soft tissue processor 32 is a contrast agent processor. The noise frame processor 30 generates an estimate of electronic or thermal noise as the noise varies over the frame in response to receive configuration associated with the contrast agent imaging. The contrast agent processor 32 generates a smoothed surface indicative of the intensity of contrast agent within an image frame of data at various locations in the frame. The gain processor 34 uses outputs from the processors 30 and 32 to adaptively adjust or determine either the average gain, depth gain, lateral gain and/or other gain parameter.

FIG. 5 provides a more detailed flow diagram of the one embodiment of the operation of the second processor 26 to determine gain from contrast agent data. Detected, log-compressed frames of data representing contrast agent and noise are used to determine a gain parameter. The flow of FIG. 5 is similar to the flow of FIG. 4, so the same acts (i.e. same reference number) using the same type or different types of data will not be repeated in this description of FIG. 5. Instead, the differences in the algorithm for determining gain parameters for contrast agent data are described below.

The binary mask of act 60 is determined independent of a variance calculation of the contrast agent data. The binary mask is free of any variance parameter of the contrast agent data. Masking based on variance is unreliable due to the statistical properties of data representing contrast agent. For contrast agent data with minimal or no tissue information, the unreliability is even greater. Prior to injection of contrast agent, data representing contrast agent may not provide any variance information. The variance information is bypassed, and the SNR information is used for identifying regions or spatial locations for masking as discussed above for act 60. In alternative embodiments, the data representing contrast agents may be further used for masking. For example, variance information is determined after injection of contrast agent. As another example, a different characteristic of the data representing contrast agent that accounts for the statistical properties of the data is used. In cardiology imaging, signal levels of data representing contrast agent in the ventricle are generally greater than signal levels of contrast agent in the myocardium. The binary mask may be used to exclude spatial locations representing the ventricle by applying an upper or maximum signal level threshold to the contrast agent data, applying an upper signal level threshold to signal-to-noise ratio data, applying an adaptive threshold based on the peak signal levels, or by using a distinct imaging method or detection technique which identifies the ventrical, as described below.

Another difference is the process after the test for a sufficient number of tissue regions of act 61 (FIG. 4), 63 (FIG. 5). In act 63, the contrast agent data is tested for a sufficient number of contrast agent regions. Similar spatial and/or signal tests as discussed above for act 61 may be used. Other tests based on expected contrast agent imaging characteristics may be used. The outcome of this test is different depending on whether contrast agents are present within the field of view. Prior to injection of contrast agents, data representing contrast agents includes minimal or no signal, in which case optimization of gain for maximum sensitivity based on thermal noise is advantageous. However, signals from non-contrast agent sources, such as from tissue, may be non-negligible and will obstruct the ability to image contrast agents. Adjusting gain without regard to tissue leakage results in a lesser sensitivity to contrast agent. Identifying the pre-contrast state allows gain to be set for maximal sensitivity even in the presence of tissue signal leakage. Sensitivity is important in contrast agent imaging. The gain and associated signal mapping is ideally set to maximize sensitivity to contrast agent signals.

Unlike the algorithm of FIG. 4, the process of FIG. 5 continues if an insufficient number of contrast agent regions are identified. The arrow 65 indicates the process where the test finds an insufficient number. Act 84 is replaced with act 85. In act 85, the gain parameters output by act 80 are used as the final gain parameters. The gain of the system is adaptively varied based on the noise values without calculating or using gain parameters calculated from the contrast agent data. Using the noise based gain parameter, the noise values are mapped within the image to a substantially constant low value, such as a zero value at or a value below the dynamic range. The noise target value of act 80 is selected such that a uniform dim signal level is provided prior to injection of contrast agents. The noise is mapped to a dim value within or lower than the dynamic range of the system. Gain parameters that result in a constant low level of noise throughout the image or field of view provide maximum sensitivity to any signal. Once contrast agents are injected, the gain provides a greater sensitivity to the resulting contrast agent signals. By using the gain parameters associated with the noise information prior to injection of contrast agents, an optimal gain is provided for imaging contrast agents before and after injection. The injection of contrast agents is not tracked or needed to trigger further gain adjustments.

In alternative embodiments, the gain is adjusted for maximum sensitivity by using a stored gain. For example, stored gain parameters representing expected noise levels are used if insufficient contrast agent signal is found in the test of act 63. In other alternative embodiments, the gain is adjusted for maximum sensitivity by calculating expected noise.

If the gain is being set after the injection of contrast agents, setting the gain parameters to provide a uniform dim brightness is unacceptable. Contrast agent signal information would be lost. Instead, the gain parameters are determined in a manner similar to setting for tissue imaging. Regions associated with contrast agents are treated as regions associated with soft tissue. Identification of a sufficient number of regions in act 63 indicates that contrast agent has been injected within the field of view. If a sufficient number of contrast agent regions are identified, acts 62 and 64 are performed using the contrast agent data. The target value for the contrast agent data is similar to or different than the tissue target value. For example, a greater value associated with a brighter mapping level emphasizes contrast agent. In act 85, like act 84, the minimum or other function is used to select between gain parameters from the contrast agent data and the noise data.

Other algorithms using the same or different inputs and processes may be used for adaptively determining one or more gain parameters for the contrast agent or other data. For example, a stored average gain or gain curve is applied for contrast agent imaging prior to injection of contrast agent. The stored gain information provides a desirable or likely gain usable before and while imaging contrast agents in the field of view. In other embodiments, the stored gain information is used after the presence of contrast agents is determined.

The target values or other inputs for the contrast agent data may be different or the same as for different types of imaging. In alternative embodiments, the target value for the noise data and/or for the contrast agent data varies as a function of the presence of contrast agent. For contrast agent data that includes a substantial amount of tissue information, such as second harmonic B-mode contrast agent imaging, the presence of contrast agent for spatial locations in the field of view is determined. In one embodiment, the number of regions and distribution of regions of contrast signals is determined, such as discussed above for act 63. Other calculations are possible. For example, the number of regions with an average signal-to-noise ratio above a threshold indicates the presence of contrast agents. As another example, the number of regions where the average signal-to-noise ratio is above a threshold and the local variance of the contrast agent data is within a threshold range of values indicates the presence of contrast agents. As yet another example, the average or other signal-to-noise ratio values are compared to a threshold determined based on the current imaging configurations (e.g. transducer, frequency of operation and type of contrast agent). User input may be used to indicate the presence of contrast agent. A time trigger may also be used, such as determining the presence based on an amount of time after injecting contrast agents. An increase in or the rate of increase of the signal-to-noise ratio as a function of time may also indicate the presence of contrast agent.

The gain parameter algorithm is optimized as a function of the presence of contrast agents. If no or little contrast agent is present, the target value is selected to map the data to a low constant value, such as associated with a dim brightness. For example, a target value applied to the contrast agent data is set to provide a uniform brightness for a resulting image. Tissue information is mapped as noise. If contrast agent is present, the target value is selected to provide a user desired brightness for spatial locations associated with contrast agent. In addition or an alternative to adapting the target value, the algorithm used or another variable are adapted as a function of the presence of contrast agent in the field of view.

Rather than determining the gain parameters once or in response to one trigger, other embodiments continually or periodically determine and apply gain parameters. For example, gain parameters are determined in response to initiation of imaging or after a delay and then reapplied once the presence of contrast agents are determined. Any of time or event based triggers may be used to determine gain parameters a first or subsequent times.

The gain parameters responsive to one, two or more types of imaging are used to determine the final gain for each spatial location in an image. The resolve processor 28 as shown in FIG. 2 receives the gain parameters. In one embodiment, an average gain and a two-dimensional gain curve are provided for each type of imaging. In alternative embodiments, a two-dimensional gain curve representing a combination of the average gain and spatial variance in the gain is provided. In yet other alternative embodiments, only depth or lateral gain curves or an average gain are provided. Other gain parameters may be used.

The resolve processor 28 synthesizes the gain parameters. At least one of the gain parameters is selected. In one embodiment, the average tissue gain and average contrast agent gain are both selected and output separately. The resolve processor 28 operates on two spatially varying functions, so in that sense operates locally. The weighting or decision about how to combine the multiple gain curves is performed as a global parameter. For example, the same weight is used throughout the image. Alternatively, the combination is dependent on specific locations within an image. The determination of whether contrast is present may be performed locally or globally for an entire image. For global determination, the presence of contrast agent within any region of the image is determined.

The two-dimensional gain curve (LGC and DGC) for each region is selected based on the type of display or independent of the type of display. For displaying just the contrast agent image, just the tissue image or a combination of both images, a gain curve is selected for application to the entire image. The user selects the type or types of images to be displayed. One of the contrast agent gain, tissue gain, a minimum of the contrast agent and tissue gains or a weighted average of the contrast agent and tissue gains is selected based on the type of imaging. The weighted averaging combines the LGC and/or DGC parameters for each type of imaging. The gain parameters are each weighted and then the weighted gains are summed. The same (e.g. average) or different weights may be used to emphasize one gain over another. Where the combination is non-linear, such as selecting the minimum, maximum or other non-linear function, the resulting gain curve is normalized. For example, the average gain of the curve is set to a zero value and the associated offset is applied to the master or average gain.

In alternative embodiments, the average gains are combined or only one selected so that the average gains are not independently controlled. In yet other alternative embodiments, the LGC and/or DGC gain curves are selected and output separately for independently controlling the gain of data for two different types of imaging. In other embodiments, the spatially varying and average gain are combined as one gain parameter for input and/or output from to the resolve processor 28.

The final gain parameters are applied to the data for generating an image. The average gain and gain of the two-dimensional curve are added to the data. If the image includes data for both types of imaging, different gain parameters are applied to the different types of data. For example, different average gains are applied for contrast agent data than for tissue data, but the same LGC and/or DGC gain curves are applied. The gain corrected data is then used to generate an image. The image responsive to data for one or more types of imaging and one or more gain parameters is displayed.

Additional types of imaging may be used, such as detecting tissue or fluid motion. The additional type of imaging is used in combination with the one or two other types of imaging, such as tissue and contrast agent imaging. Motion imaging may share or use separate transmit and/or receive information as other types of imaging. For example, the contrast agent imaging transmits three beams of acoustic energy with interpulse amplitude and phase modulation represented as [½–1½]. The received pulses are equally weighted without phase inversion [1 1 1]. For motion, three pulses are transmitted with the same amplitude and relative phase [1 1 1]. The received pulses are combined with weights, such as [½–1½]. The amplitude of the combined receive signals is detected. In cardiology imaging, the detected motion may identify the ventricle for masking the contrast agent data as part of determining the gain. The resulting contrast agent gain parameters are set based on contrast agent data associated with the myocardium, the region of interest.

In another alternative embodiment, the contrast agent imaging is altered to include tissue information. For example, for contrast agent imaging, three beams of acoustic energy are transmitted with interpulse amplitude and phase modulation represented as [½–1½]. The received pulses are not equally weighted, such as receive weights of [1 0.95 1], allowing some tissue information to leak through. The tissue information provides sufficient signal so that acts 62 and 64 are more likely used to determine gain parameters even without contrast agent in the field of view.

In other embodiments, one or more aspects of the process of FIG. 5 are used for generating images responsive to only one type of imaging. For example, the gain parameters are determined without masking in response to variance, or the presence of contrast agent is determined. Types of imaging using these or other aspects include Coherent Contrast Imaging™ (i.e. alternate scan line phasing) pulse or phase inversion imaging as described in U.S. Pat. Nos. 5,951,478 and 5,632,277, pulse inversion Doppler imaging as described in U.S. Pat. No. 6,095,980, power modulation imaging as described in U.S. Pat. No. 5,577,505, or other imaging techniques including tissue and/or contrast agent information. The above listed U.S. Patents are incorporated herein by reference.

In yet another embodiment, anatomy is identified and used to mask data for the gain decision. For example, data is formed using a loss-of-correlation sequence (e.g. transmit weights of [1 1 1] and receive weights of [1–2 1]). A threshold is applied to identify anatomy from the loss-of-correlation data, such as the ventricle in cardiology imaging. Data above a threshold or within a threshold range is identified as the anatomy. Data corresponding to spatial locations associated with the anatomy are removed from the gain parameter determination.

For example, additional data is formed in response to different sequence (e.g. transmit weights of [½–1½] and receive weights of [1 1 1]). Alternatively, the same loss-of-correlation data is used. The data is masked to exclude information corresponding to the identified anatomy. The masked data is used to determine the gain parameters. An image is generated from the loss-of-correlation data, the additional data or other data in response to the gain parameter.

While the invention has been described above by reference to various embodiments, it should be understood that many changes and modifications can be made without departing from the scope of the invention. For example, only one type of imaging is used, such as contrast agent imaging. The embodiment of FIG. 5 or another algorithm determines the gain for the contrast agent imaging. The gain may be determined using one type of data, but applied for imaging with a different type of data. A different transmit sequence is used or yet another recombination of data is performed for imaging than is used for determining the gain.

It is therefore intended that the foregoing detailed description be understood as an illustration of the presently preferred embodiment of the invention, and not as a definition of the invention. It is only the following claims, including all equivalents, that are intended to define the scope of this invention.

What is claimed is:

1. In a medical diagnostic imaging system, a method for adaptively controlling gain in an image, the method comprising:

(a) determining a first gain parameter in response to first data;

(b) determining a second gain parameter in response to second data, the first data different than the second data;

(c) selecting at least one of the first and second gain parameter; and (d) displaying an image based on at least one of the first and second data and responsive to the selected gain parameter.

2. The method of claim 1 wherein (c) comprises selecting both the first and second gain parameter;

further comprising:

(e) combining the first and second gain parameters; and wherein (d) comprises displaying the image responsive to the combined first and second gain parameters.

3. The method of claim 2 wherein (e) comprises:

(e1) weighting the first and second gain parameters; and (e2) adding the weighted first and second gain parameters.

4. The method of claim 1 wherein (a) comprises determining the first gain parameter in response to first data representing tissue and (b) comprises determining the second gain parameter in response to second data representing contrast agents.

5. The method of claim 1 wherein (a) and (b) comprises determining the first and second gain parameters in response to different types of imaging.

6. The method of claim 1 wherein (a) comprises determining the first gain parameter such that first average amplitudes of areas of soft tissue of the first data are substantially at a first target display value and (b) comprises determining the second gain parameter such that noise values are mapped within the image to a substantially constant low value.

7. The method of claim 1 wherein (a) and (b) comprise fitting a surface to the first and second data, respectively.

8. The method of claim 1 wherein (a) comprises determining the first gain parameter as a function of first noise values and in response to variances of the first data, and wherein (b) comprises determining the second gain parameter as a function of second noise values and independent of variances of the second data.

9. The method of claim 1 wherein (a) comprises setting first gains for spatial locations in the image representing soft tissue and (b) comprises setting second gains for spatial locations in the image representing contrast agent;

further comprising:

(e) determining a presence of contrast agent for the spatial locations in the image representing contrast agent;

wherein (b) further comprises adaptively varying the second gains in response to noise values if the presence corresponds to a lack of contrast agents and adaptively varying the second gains in response to noise values and contrast agent values if the presence corresponds to contrast agents.

10. The method of claim 1 further comprising:

(e) determining a presence of contrast agent within a two-dimensional region as a function of the second data; and (f) adaptively varying the second gain parameter of the system based on the presence.

11. In a medical diagnostic imaging system, a method for adaptively controlling gain in an image, the method comprising:

(a) determining noise values at a plurality of locations in a region;

(b) adaptively varying a gain of the system based on the noise values, the gain associated with mapping the noise values within an image to a substantially constant low value; and (c) generating an image of contrast agent responsive to the gain.

12. The method of claim 11 wherein (b) comprises maximizing sensitivity.

13. The method of claim 11 wherein the low value is a constant value within a dynamic range of the image.

14. The method of claim 11 wherein the low value is below the displayed dynamic range.

15. The method of claim 11 wherein (a) and (b) comprise determining a first gain parameter in response to first data of a first type of imaging;

further comprising:

(d) determining a second gain parameter in response to second data of a second type of imaging, the second type of imaging different than the first type of imaging; and (e) selecting at least one of the first and second gain parameter;

wherein (c) comprises displaying an image based on the first and/or second data and responsive to the selected gain parameter.

16. The method of claim 15 wherein (e) comprises selecting both the first and second gain parameter;

further comprising:

(f) combining the first and second gain parameters; and wherein (c) comprises displaying the image responsive to the combined first and second gain parameters.

17. The method of claim 11 wherein (b) comprises fitting a surface to the noise values.

18. The method of claim 11 wherein (b) comprises adaptively varying the gain independent of variances of data representing the contrast agent.

19. The method of claim 11 further comprising:

(d) determining a presence of contrast agent within the image;

wherein (b) further comprises adaptively varying the gain in response to noise values if the presence corresponds to a lack of contrast agents and adaptively varying the second gains in response to noise values and contrast agent values if the presence corresponds to contrast agents.

20. In a medical diagnostic imaging system, a method for adaptively controlling gain in an image of contrast agents, the method comprising:

(a) detecting first data representing a two-dimensional region;

(b) determining spatial locations represented by the first data associated with noise;

(c) masking the first data as a function of the spatial locations associated with noise; and (d) adaptively varying a gain of the system based in at least part on the masked first data.

21. The method of claim 20 wherein (c) comprises masking free of a variance parameter of the first data.

22. The method of claim 20 wherein (a) comprises detecting contrast agents.

23. The method of claim 20 wherein (d) comprises adaptively varying the gain of the system based on the noise values, the gain associated with mapping the noise values within the image to a substantially constant low value; and further comprising:

(e) generating an image of contrast agent responsive to the gain.

24. The method of claim 20 wherein (d) comprises varying a gain in response to first data of a first type of imaging;

further comprising:

(e) determining a second gain parameter in response to second data of a second type of imaging, the second type of imaging different than the first type of imaging;

(f) displaying an image based on at least one of the first and second data and responsive to (d) and the second gain parameter.

25. The method of claim 20 wherein (a) comprises detecting contrast agents; and further comprising:

(e) determining a presence of contrast agent for spatial locations within the two-dimensional region;

wherein (d) comprises adaptively varying the gain in response to noise values if the presence corresponds to a lack of contrast agents and adaptively varying the gain in response to the noise values and contrast agent values if the presence corresponds to contrast agents.

26. In a medical diagnostic imaging system, a method for adaptively controlling gain in an image of contrast agents, the method comprising:

(a) detecting first data representing a two-dimensional region;

(b) determining a presence of contrast agent within the two-dimensional region as a function of the first data; and (c) adaptively varying a gain of the system based on the presence.

27. The method of claim 26 further comprising:

(d) displaying an image as a function of the gain and second data, the second data different than the first data.

28. In a medical diagnostic imaging system, a method for adaptively controlling gain in an image, the method comprising:

(a) determining a first gain parameter in response to first data;

(b) determining a second gain parameter in response to second data, the first data different than the second data;

(c) selecting at least one of the first and second gain parameter; and (d) displaying an image responsive to the selected gain parameter.

29. In a medical diagnostic imaging system, a method for adaptively controlling gain in an image, the method comprising:

(a) determining a mask in response to first data;

(b) masking second data with the mask, the first data different than the second data;

(c) determining a gain parameter in response to the masked second data; and (d) displaying an image responsive to the selected gain parameter.

30. The method of claim 29 wherein (d) comprises displaying the image responsive to the second data.

31. The method of claim 29 wherein (a) comprises identifying anatomy and (c) comprises determining the gain parameter in response to second data representing the identified anatomy.

* * * * *